(12) United States Patent
Jessop

(10) Patent No.: US 9,955,685 B2
(45) Date of Patent: *May 1, 2018

(54) COATING COMPOSITION FOR PATHOGEN CONTROL IN SOYBEAN

(75) Inventor: Nicholas Hugh Hylton Jessop, Winchester (GB)

(73) Assignee: Exosect Limited, Winchester, Hants (GB)

( * ) Notice: Subject to any disclaimer, the term of this patent is extended or adjusted under 35 U.S.C. 154(b) by 50 days.

This patent is subject to a terminal disclaimer.

(21) Appl. No.: 14/112,647

(22) PCT Filed: Apr. 19, 2012

(86) PCT No.: PCT/GB2012/000357
§ 371 (c)(1),
(2), (4) Date: Nov. 13, 2013

(87) PCT Pub. No.: WO2012/143675
PCT Pub. Date: Oct. 26, 2012

(65) Prior Publication Data
US 2014/0057787 A1    Feb. 27, 2014

(30) Foreign Application Priority Data

Apr. 20, 2011 (GB) .................. 1106744.4

(51) Int. Cl.
| | |
|---|---|
| *A01N 25/08* | (2006.01) |
| *A01N 63/04* | (2006.01) |
| *A01N 25/12* | (2006.01) |
| *A01N 25/00* | (2006.01) |
| *C09D 191/06* | (2006.01) |
| *A01N 25/24* | (2006.01) |
| *A01N 25/10* | (2006.01) |
| *A01N 25/14* | (2006.01) |
| *A01N 43/36* | (2006.01) |
| *A01N 51/00* | (2006.01) |
| *A01N 63/00* | (2006.01) |
| *C09D 5/14* | (2006.01) |

(52) U.S. Cl.
CPC ............. *A01N 25/12* (2013.01); *A01N 25/00* (2013.01); *A01N 25/10* (2013.01); *A01N 25/14* (2013.01); *A01N 25/24* (2013.01); *A01N 43/36* (2013.01); *A01N 51/00* (2013.01); *A01N 63/00* (2013.01); *C09D 5/14* (2013.01); *C09D 191/06* (2013.01)

(58) Field of Classification Search
None
See application file for complete search history.

(56) References Cited

U.S. PATENT DOCUMENTS

| | | | | |
|---|---|---|---|---|
| 3,905,152 | A * | 9/1975 | Loperfido | ............... A01C 1/06 47/57.6 |
| 4,251,952 | A * | 2/1981 | Porter | ...................... A01C 1/06 47/57.6 |
| 4,297,339 | A |  10/1981 | Craven | |
| 4,879,839 | A * | 11/1989 | Gago | ........................ A01C 1/06 427/4 |
| 5,283,060 | A |  2/1994 | Shieh | |
| 6,221,375 | B1 * | 4/2001 | Howse | .......................... 424/417 |
| 2007/0072775 | A1 | 3/2007 | van Boxtel-Verhoeven et al. | |
| 2007/0207927 | A1 | 9/2007 | Rosa et al. | |
| 2009/0306060 | A1 * | 12/2009 | Watrin | ................... A01N 37/46 514/229.2 |
| 2010/0112060 | A1 * | 5/2010 | Maor et al. | ................... 424/484 |
| 2010/0291231 | A1 | 11/2010 | Stadler et al. | |
| 2010/0317523 | A1 * | 12/2010 | Ikeda | ..................... A01N 43/78 504/223 |
| 2012/0324604 | A1 * | 12/2012 | Dutton et al. | ................. 800/298 |
| 2013/0101655 | A1 * | 4/2013 | Storm et al. | .................. 424/409 |

FOREIGN PATENT DOCUMENTS

| | | | |
|---|---|---|---|
| DE | 199 06 491 A1 | 8/2000 | |
| EP | 2 229 808 A1 | 9/2010 | |
| JP | 5-205226 A | 11/1993 | |
| WO | 01/78509 A2 | 10/2001 | |
| WO | 2005/077169 A1 | 8/2005 | |
| WO | 2007/072046 A2 | 6/2007 | |
| WO | 2008/062221 A2 | 5/2008 | |
| WO | WO-2009124707 A2 * | 10/2009 | ............. A01N 63/00 |
| WO | WO 2010106314 A2 * | 9/2010 | ............. A01N 25/22 |
| WO | WO-2010107312 A1 * | 9/2010 | ............... A01C 1/06 |
| WO | 2011/128639 A2 | 10/2011 | |
| WO | 2011/128639 A2 | 12/2011 | |

OTHER PUBLICATIONS

G. Harish et al., "Evaluation of biorational pesticides against lepidopteran defoliators in soybean," Karnataka J. Agric. Sci., 22(4): 914-917 (2009).*
W. Hu et al., "Pathogenicity of Beauveria bassiana to Riptortus linearis (Hemiptera: Coreidae), a Pest of Soybean," Appl. Entomol. Zool. 31(2): 187-194 (1996).*
"Solid," <https://www.merriam-webster.com/dictionary/solid>, © 2017 Merriam-Webster, incorporated, p. 2.*
International Search Report for PCT/GB2012/000357 dated Dec. 17, 2012.
Search Report for GB1206948.0 dated Aug. 17, 2012.

* cited by examiner

*Primary Examiner* — Tracy Vivlemore
*Assistant Examiner* — Monica A Shin
(74) *Attorney, Agent, or Firm* — Sughrue Mion, PLLC

(57) ABSTRACT

Coating composition for soya bean seed from which roots and shoots are capable of growing, wherein the coating composition comprises an organic carrier material and one or more biological agents that possess an activity against at least one or more pathogens of the soybean plant.

21 Claims, 1 Drawing Sheet

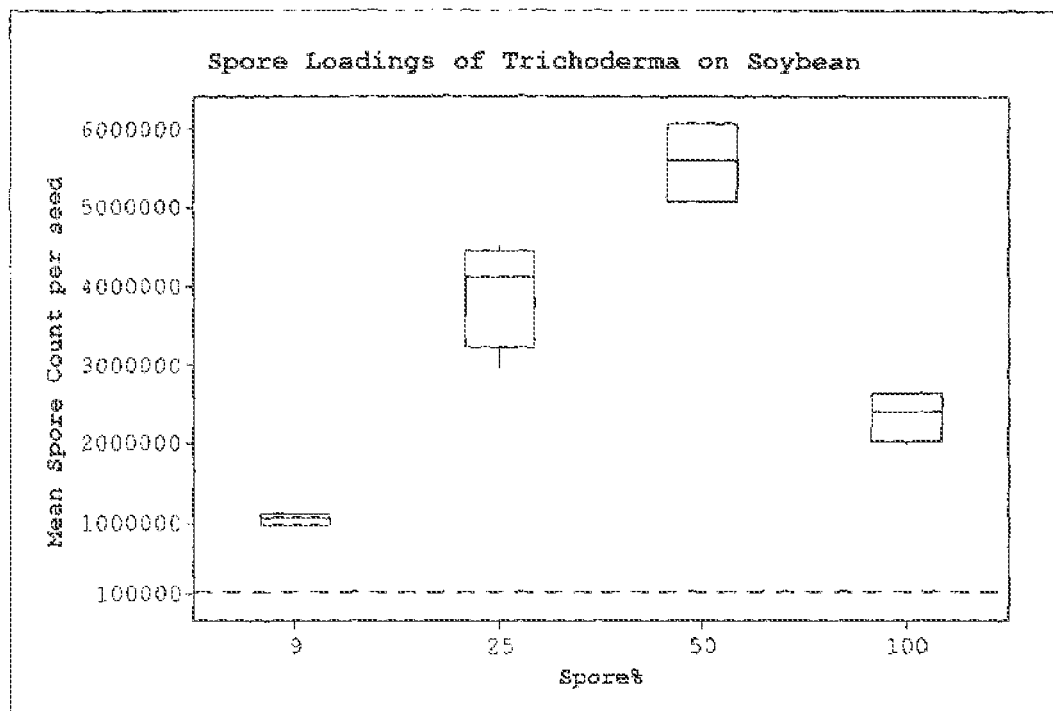

COATING COMPOSITION FOR PATHOGEN CONTROL IN SOYBEAN

CROSS REFERENCE TO RELATED APPLICATIONS

This application is a National Stage of International Application No. PCT/GB2012/000357 filed Apr. 19, 2012, claiming priority based on British Patent Application No. 1106744.4 filed Apr. 20, 2011, the contents of all of which are incorporated herein by reference in their entirety.

The present invention relates to coating compositions including an organic component and a biological agent for applying to soybean seed from which roots and shoots are capable of growing, uses of coating compositions on soybean plant seeds, methods of producing such coating compositions and seeds coated with such coating compositions. In particular, the invention relates to coating compositions that comprise an organic carrying material and biological agents selected from chemicals and live biological agents active against one of more plant pathogens selected from bacterial, fungal and arthropod pathogens that infest seeds of soybean plants.

Losses in yield in soybean crops are recorded annually and come about as a result of plant infestations due to pathogens such as bacteria, fungi and arthropods which can infest the plants at various stages of development, such as at the seed stage. Agronomic losses due to pathogen infestations remain high despite many defensive measures that have been devised by man to combat such infestations. Such defensive measures include the use of synthetic chemicals; the employment of genetic engineering of soybean plants; and the use of live biological agents that are applied in the form of coatings, sprays and washes to seeds.

Pesticides in the form of chemical agents such as fungicides, bactericides and arthropodicides, typically in the form of insecticides and/or acaricides may be applied to soybean crops in the form of soil drenches, liquid seed treatments and the like. Such kinds of chemical treatments tend to be indiscriminate in their action and may adversely affect beneficial bacteria, fungi and arthropods as well as the plant pathogens at which such treatments are targeted.

When conventional pesticides are used as seed treatments the seeds are coated with pesticide directly or the pesticide is applied to the seed in the presence of an inorganic carrier. Such seed treatments are typically applied in liquid form or as wet slurry and subsequently the seeds are dried. Such treatments are mostly aimed at providing direct protection against pathogens such as arthropods and/or seed borne microorganisms and/or soil borne microorganisms that attack the seed. The high level of chemicals that are typically used introduces a chemical load to the environment that may give rise to ecological concerns.

One problem in applying a biological agent that is a chemical agent in conventional seed coating procedures is that the chemical agent is typically applied as slurry and this may give rise to an uneven application of the coating whereby the seeds are not fully coated or a percentage of the seeds, up to 20% depending on seed type and the coating procedure employed, do not get fully coated. Furthermore, the seed coatings may not be uniform and this gives rise to physical weaknesses in the seed coat and the coating may flake off.

A further problem arises when using biological agents that are selected from beneficial live bacterial and fungal species that may be applied conventionally to seeds, for example as spores in conjunction with an inorganic carrier in the form of particulate compositions or in the form of liquid compositions which may then be dried back, is that the applied biological agents rapidly lose viability. Without the intention of being bound by theory, it is thought that as the seeds are dried off the micro-environment alters and the viability of applied live biological agents may be seen to decrease sharply and almost as soon as the applied composition dries. The loss of viability of the biological agent is typically associated with the splitting of the fungal or bacterial spores which renders them non-viable.

It has now been found that by using an organic carrier material in conjunction with a biological agent, the viability of the biological agent is improved on soybean seeds, relative to the viability of biological agents applied to such seeds conventionally. Furthermore, the seed coating is less susceptible to flaking off.

It is an object of the present invention to supply improved seed coatings comprising biological agents for soybean seeds. Furthermore, it is an object of the invention to supply seed coatings that utilise fewer chemical additives and/or lesser amounts of thereof for protecting seed and/or young plantlets from pathogens than conventional seed coatings.

These and other objects of the invention will become apparent from the following description and examples.

According to the present invention there is provided a soybean seed coating composition, wherein the said coating composition comprises at least one organic carrier material in the form of particles wherein the carrier material is selected from waxes having a melting point of $\geq 50°$ Centigrade and one or more biological agents that possess an activity against one or more pathogens of a soybean plant.

The soybean seed coating composition is applied to soybean plant seeds from which roots and shoots are capable of growing. For the purposes of the present invention a soybean seed is one from which roots and shoots are able to grow. Reference to "seed" and "seeds" is used interchangeably herein and means soybean seeds that are viable to which compositions of the invention may be applied.

The organic carrier material is selected from organic materials that can be applied to soybean seeds preferably as a dry powder wherein the powder particles are of a predetermined volume mean diameter or in liquid form, such as an oleaginous formulation or as an aqueous formulation.

Generally, the composite particles of use in a dry powder composition of the invention possess a volume mean diameter of a certain size as defined herein. To obtain particles of organic materials of a volume mean diameter applicable for use in the invention, organic materials in the form of, for example, 1 to 5 kilogram blocks or tablets may be broken up or kibbled into small millimeter-sized pieces (such as from 2 mm-8 mm approximate diameter in size, for example from 4 mm to 6 mm) in a kibbling machine. The millimeter-sized pieces can then be passed through a comminuting means such as a standard mill, e.g. an Apex Comminuting mill, and milled or comminuted into particles having an approximate diameter in the range from 100 µm-500 µm, for example from 250 µm-300 µm. The micron-sized comminuted particles can then be passed through a micronising apparatus, such as an AFG micronising air mill to obtain particles of a desired VMD range, such as from 15 µm-20 µm, that is of use in the present invention. The skilled addressee will appreciate that such procedures for obtaining small particles are well known in the art. Preferably, dry powder compositions of the invention comprise composite particles having a volume mean diameter of 5 µm, for example of 8 µm, 9 µm, 10 µm, 11 µm, 12 µm, 13 µm, 14 µm, 15 µm up to 40 µm or any value there inbetween. As stated herein, the volume mean diameter of the composite particles is typically ≥10 μm or ≥12 μm and may lie in the range from 10 μm to 200 μm and may have a value that lies anywhere there inbetween, for example from ≥10 μm to 100 μm; or from ≥10 μm to 40 μm; or from ≥10 μm to 30 μm or any desired volume mean diameter value in between. Preferably, dry powder compositions of the invention comprise particles having a volume mean diameter of ≥8 μm, for example of 8 μm, 9 μm, 9.7 μm, 10 μm, 11 μm, 12 μm, 13 μm, 14 μm, 15 μm and the like up to any volume mean diameter of choice, such as up to 200 μm or any volume mean diameter in between for example 40 μm or 30 μm. Particles of the invention that possess a volume mean diameter ≥10 μm are considered to be less of a thoracic hazard to humans and are not thought to be allergenic.

In liquid formulations, particles of a pre-determined volume mean diameter are suspended therein in a suspension formulation and applied to the seeds which are then dried using conventional drying procedures. Where the organic carrier material is applied to soybean seeds in a dry powder form, the particles of the organic carrier material may have a volume mean diameter of any conventional size, as herein described. To such dry powders, chemicals of use against arthropod pathogens such as insects, arachnids and if appropriate, their larvae, eggs, or pupae; chemicals of use against bacterial pathogens; and chemicals of use against fungal pathogens may be added prior to the coating of soya bean seed. Additionally, beneficial live biological agents may be added to such dry powders of use in the present invention, the live biological agents being able to target bacterial pathogens of the soya bean plant and/or to target fungal pathogens and/or arthropods of the soya bean plant. Spores of choice of beneficial live biological agents such as fungal conidia or hyphae or mycelia of fungi that do not form spores or conidia-like structures may be added to dry powders of use in the present invention. Suitable organic carrier materials of use in the invention are typically made up of organic materials such as waxes having a melting point of ≥50° C., more preferably of ≥60° C., and most preferably are made up of hard waxes having a melting point of ≥70° C.

Natural waxes of use in the present invention include carnauba wax, beeswax, Chinese wax, shellac wax, spermaceti wax, myricyl palmitate, cetyl palmitate, candelilla wax, castor wax, ouricury wax, wool wax, sugar cane wax, retamo wax, rice bran wax and the like.

Synthetic waxes of use in the present invention include suitable waxes selected from paraffin wax, microcrystalline wax, Polyethylene waxes, Fischer-Tropsch waxes, substituted amide waxes, polymerized α-olefins and the like.

Mineral waxes of use in the invention include montan wax (e.g. Lumax® Bayer) ceresin wax, ozocerite, peat wax and the like.

Suitable organic carrier particles may be selected from waxes such as carnauba wax, beeswax, montan wax, Chinese wax, shellac wax, spermaceti wax, myricyl palmitate, cetyl palmitate, candelilla wax, castor wax, ouricury wax, wool wax, sugar cane wax, retamo wax, and rice bran wax or a mixture of two or more thereof. Such waxes typically display a high enthalpy of lattice energy during melt. Preferably the organic carrier material is carnauba wax which may be applied in liquid form, typically in the form of a suspension of particles, or more preferably, in powder form as discrete particles. Generally, the particles of use in the invention possess a volume mean diameter as herein described.

Additionally, the organic carrier particles of use in compositions of the invention may contain other components such as additives selected from UV blockers such as beta-carotene or p-amino benzoic acid, colouring agents such as optical brighteners and commercially available colouring agents such as food colouring agents, plasticisers such as glycerine or soy oil, antimicrobials such as potassium sorbate, nitrates, nitrites, propylene oxide and the like, antioxidants such as vitamin E, butylated hydroxyl anisole (BHA), butylated hydroxytoluene (BHT), and other antioxidants that may be present, or mixtures thereof. The skilled addressee will appreciate that the selection of such commonly included additives will be made depending on end purpose, and perceived need.

Liquid formulations of the invention may be formulated as an aqueous formulation or as an oleaginous formulation, depending on design. Aqueous formulations may include surfactants selected from commercially available surfactants such as Libsorb, Silwet L77, Tween 80, Torpedo II, Newmans T80, Fortune, Guard, Rhino, Biopower, and the like.

Oleaginous formulations, that is to say oil-based formulations, may contain any oil suitable for use in the present invention which may be selected from petroleum oils, such as paraffin oil, and vegetable oils such as rapeseed oil, soybean oil, sunflower oil, palm oil and the like. Oil formulations of use in the invention contain organic carrier particles as described herein and these in turn may be admixed with flow agents such as hydrophilic precipitated silicas, for example Sipernat 383 DS, Sipernat 320, EXP 4350, and Sipernat D-17 and the like. Such free-flowing agents may be dispersed in oils, for example, for anti-foaming purposes.

The skilled addressee will appreciate that where an aqueous or an oil formulation may be used to apply biological agents of use in the invention, the liquid element should be removed from the coated seed after coating is achieved, for example by drying off using conventional drying processes, leaving a seed coating composition in dry particulate form, wherein the seed coating composition is made up of the organic carrier as herein described and the at least one biological agent, also as herein described.

A biological agent for the purposes of the present invention is one that can be used to control the population of a plant pathogen of a soya bean plant, and may be selected from chemical fungicides, arthropodicides such as insecticides and acaricides, bactericides and from live biological agents that are able to control the population of one or more seed or soil borne pathogens of a soybean plant seed. Preferably, the population of the soil borne pathogen on or in the immediate vicinity of the soybean plant seed is reduced either by the biological agent rendering it unable to reproduce and/or by killing it. Examples of biological agents of use in the present invention include chemicals for use on soybean plant seeds selected from arthropodicides, such as insecticides and acaricides, fungicides and bactericides commonly employed in the art. Suitable examples of such chemicals include nicotinoid insecticides such as imidacloprid [(E)-1-(6-chloro-3-pyridylmethyl)-N-nitroimidazolidin-2-ylideneamine and, Thiamethoxam (EZ)-3-(2-chloro-1,3-thiazol-5-ylmethyl)-5-methyl-1,3,5-oxadiazinan-4-ylidene(nitro)amine and the like.

Suitable fungicides for use on seeds in accordance with the invention include those selected from acyl amino acid fungicides such as mefenoxam [methyl N-(methoxyacetyl)-N-(2,6-xylyl)-D-alaninate], pyrrole fungicides such as fludioxinil [4-(2,2-difluoro-1,3-benzodioxol-4-yl)-1H-pyrrole-3-carbonitrile], strobilurin fungicides such as azoxystrobin

[methyl (2E)-2-{2-[6-(2-cyanophenoxy)pyrimidin-4-yloxy]phenyl}-3-methoxyacrylate], phthalimide fungicides such as captan [N-(trichloromethylthio)cyclohex-4-ene-1,2-dicarboximide], anilide fungicides such as carboxin [5,6-dihydro-2-methyl-1,4-oxathiine-3-carboxanilide], aromatic fungicides such as chloroneb [1,4-dichloro-2,5-dimethoxybenzene], dithiocarbamate fungicides such as maneb [manganese ethylenebis(dithiocarbamate) (polymeric)], oxazole fungicides such as oxadyxil [2-methoxy-N-(2-oxo-1,3-oxazolidin-3-yl)acet-2',6'-xylidide], aromatic fungicides such as PCNB [pentachloronitrobenzene], benzimidazole fungicides such as TBZ [-(thiazol-4-yl)benzimidazole or 2-(1,3-thiazol-4-yl)benzimidazole], and dithiocarbamate fungicides such as Thiram [tetramethylthiuram disulfide or bis (dimethylthiocarbamoyl)disulfide].

Formulations containing live biological agents such as bacteria for use in controlling fungal infestations in soybean include *Bacillus* spp. such as *B. subtilis* MBI600 (available from Becker Underwood Inc Micro Group Ltd., Hemel Hempstead UK) and *B. pumillus* (available from Gustafson Inc., Plano, USA).

The skilled addressee will appreciate that compositions of the invention may also be added direct to the soil or growing medium into which soybean seeds are to be planted. Such compositions may be added as powders and mixed with the soil or applied as liquid suspensions using conventional procedures.

Soil borne pathogens for the purposes of the present invention are ones that are able to colonise the seed cuticle and/or ones that populate the soil and which are capable of acting on soybean seeds. Such soil borne pathogens are typically bacteria and/or fungi. Examples of fungal pathogens that attack soybean plants include *Rhizoctonia* spp. such as *R. solani*, *Aspergillus* spp., *Pythium* spp, *Sclerotium* spp. such as *S. rolfsii*, *Fusarium* spp., *Phytophthora* spp., *Alternaria* spp., and the like.

According to a further aspect of the invention there is provided use of organic carrier particles of wax in the manufacture of a soya bean seed coating composition that includes a biological agent as defined herein above. The organic carrier particles are selected from natural waxes, synthetic waxes, and mineral waxes having a melting point of ≥50° C., more preferably of ≥60° C., and most preferably are made up of hard waxes having a melting point of ≥70° C. Suitable waxes of use in this aspect of the invention may be selected from waxes such as carnauba wax, beeswax, montan wax, Chinese wax, shellac wax, spermaceti wax, myricyl palmitate, cetyl palmitate, candelilla wax, castor wax, ouricury wax, wool wax, sugar cane wax, retamo wax, and rice bran wax or a mixture of two or more thereof. Preferably, the seed coating that is employed in this aspect of the invention includes carnauba wax as the organic carrier. Preferably, in this aspect of the invention, the organic carrier particles have a mean volume diameter from ≥5 μm, such as in the range from ≥8 μm to 200 μm, as herein described.

In a third aspect of the invention there is provided use of wax as an organic carrier in particulate form in a soya bean seed coating composition as described herein. The organic carrier particles in this aspect of the invention are selected from natural waxes, synthetic waxes, and mineral waxes having a melting point of ≥50° C., more preferably of ≥60° C., and most preferably are made up of hard waxes having a melting point of ≥70° C. Suitable organic carrier particles of use in this aspect of the invention may be selected from carnauba wax, beeswax, montan wax, Chinese wax, shellac wax, spermaceti wax, myricyl palmitate, cetyl palmitate, candelilla wax, castor wax, ouricury wax, wool wax, sugar cane wax, retamo wax, and rice bran wax or a mixture of two or more thereof. Preferably, the wax carrier particles of use in this aspect of the invention comprise organic carrier particles of carnauba wax. Preferably still, the organic carrier particles of use in this aspect of the invention have a mean volume diameter ≥8 μm, such as in the range of ≥10 μm to 200 μm.

In a fourth aspect of the invention there is provided a method of manufacturing a soya bean seed coating composition as herein described that comprises
1) selecting an organic carrier material wherein the carrier material is selected from waxes having a melting point of ≥50° Centigrade;
2) comminuting said organic carrier material into particles of a desired mean volume diameter ≥5 μm, such as in the range 8 μm to 200 μm; and
3) adding biological agent to the product particles of step 2).

The biological agent of use in this aspect of the invention is selected from a chemical agent which is an arthropodicide such as an insecticide or an acaricide or a mixture thereof, or a chemical fungicide or a fungus species and/or a bacterium species or a mixture of one or more thereof.

Examples of live biological agents (also known as biocontrol organisms or biocontrol agents) that are commonly referred to in the art as "biological antagonists" that may be used in coating compositions of the present invention include include *Trichoderma* spp., *Pseudomonas* spp., and *Bacillus* spp. such as *B. subtilis* MBI600 (available from Becker Underwood Inc Micro Group Ltd., Hemel Hempstead UK) and *B. pumillus* (available from Gustafson Inc., Plano, USA) and the like.

Suitable fungicides that may be used in seed treatments on soybean seeds include those fungicides selected from acyl amino acid fungicides such as mefenoxam [methyl N-(methoxyacetyl)-N-(2,6-xylyl)-D-alaninate], pyrrole fungicides such as fludioxinil [4-(2,2-difluoro-1,3-benzodioxol-4-yl)-1H-pyrrole-3-carbonitrile] and strobilurin fungicides such as azoxystrobin [methyl(2E)-2-{2-[6-(2-cyanophenoxy)pyrimidin-4-yloxy]phenyl}-3-methoxyacrylate] and the like.

Suitable insecticides for use in seed treatments on soya beans include the nicotinoid insecticides such as imidacloprid RE)-1-(6-chloro-3-pyridylmethyl)-N-nitroimidazolidin-2-ylideneamine and, Thiamethoxam (EZ)-3-(2-chloro-1,3-thiazol-5-ylmethyl)-5-methyl-1,3,5-oxadiazinan-4-ylidene(nitro)amine such as imidacloprid [(E)-1-(6-chloro-3-pyridylmethyl)-N-nitroimidazolidin-2-ylideneamine] amine and the like.

The organic carrier material in this aspect of the invention may be selected from waxes such as from those waxes as hereinbefore described. Suitable waxes may be selected from waxes such as carnauba wax, beeswax, montan wax, Chinese wax, shellac wax, spermaceti wax, myricyl palmitate, cetyl palmitate, candelilla wax, castor wax, ouricury wax, wool wax, sugar cane wax, retamo wax, and rice bran wax or a mixture of two or more thereof. Preferably, the wax carrier particles of use in this aspect of the invention comprise dry particles of carnauba wax.

In a further aspect of the invention, there is provided a soya bean seed coating composition, such as a seed coating composition produced by the methods as described herein.

In a further aspect of the invention there is provided a coating composition as described herein for use on soya bean seeds.

In a further aspect of the invention there is provided a method of coating soybean seed with a coating composition that comprises an organic carrier material and a biological agent that has an activity against a soybean plant pathogen selected from a fungal pathogen, a bacterial pathogen and an arthropod pathogen so as to limit damage by the said pathogen to soybean plants, the method comprising adding the said biological agent to an organic carrier material wherein the organic carrier material is in dry particulate form, mixing the two components together and applying the resulting composition in dry particulate form to soya bean seeds.

The treatment composition is applied to the plant seed in dry particulate form or liquid form as hereinbefore described, and preferably in dry particulate form. Thus, the seed coating composition is applied in dry particulate form. Naturally, the skilled addressee will appreciate that the organic carrier material may also contain added pigments, plasticisers and other minor components as herein described. In an alternative, the seed coating may be applied in liquid form as herein described and then the seeds dried, leaving a coating composition that is in dry particulate form when on the seed. However, it is preferred that the coating composition is applied in dry, particulate form for ease of application and production costs are kept low. The organic carrier material in this aspect of the invention may be selected from carnauba wax, beeswax, montan wax, Chinese wax, shellac wax, spermaceti wax, myricyl palmitate, cetyl palmitate, candelilla wax, castor wax, ouricury wax, wool wax, sugar cane wax, retamo wax, and rice bran wax or a mixture of two or more thereof. Preferably, the organic carrier material is carnauba wax in dry particulate form.

The treatment composition in this aspect of the invention includes one or more biological agents selected from chemical arthropodicides such as insecticides and acaricides, fungicides, bactericides and live biological agents as herein before described.

There now follow examples that illustrate the invention. It is to be understood that the examples are not to be construed as limiting the invention in any way.

FIG. 1: Spore loadings of *Trichoderma* on soya bean

EXAMPLES SECTION

Control of *Rhizoctonia* spp. [United Kingdom National Culture Collection (UKNCC)] on soybean (*Glycine max*) by means of seed treatments using the antagonists *Trichoderma harzianum, Pseudomonas fluorescens* and *Bacillus subtilis*. [United Kingdom National Culture Collection (UKNCC)]
*Rhizoctonia* Damping-Off
Symptoms

*R. solani* primarily attacks below ground plant parts such as the seeds, hypocotyls, and roots, but is also capable of infecting above ground plant parts (e.g. pods, fruits, leaves and stems). The most common symptom of *Rhizoctonia* disease is referred to as "damping-off" characterized by non-germination of severely infected seed whereas infected seedlings can be killed either before or after they emerge from the soil. Infected seedlings not killed by the fungus often have cankers, which are reddish-brown lesions on stems and roots. In addition to attacking below ground plant parts, the fungus will occasionally infect fruit and leaf tissue located near or on the soil surface. This type of disease often occurs because the mycelium and/or sclerotia of the fungus are close to or splashed on the plant tissue. In seedlings and young plants, cotyledons and leaves wilt and drop, resulting in bare stems. In severe cases, plants die. In mildly affected plants, lower leaves develop symptoms but plants survive, but with reduced vigour.

*R. solani* can survive for many years by producing small (1 to 3-mm diameter), irregular-shaped, brown to black structures (called sclerotia) in soil and on plant tissue. *R. solani* also survives as mycelium by colonizing soil organic matter as a saprophyte, particularly as a result of plant pathogenic activity. Sclerotia and/or mycelium present in soil and/or on plant tissue germinate to produce vegetative threads (hyphae) of the fungus that can attack a wide range of food and fibre crops.

Disadvantages of Conventional Seed Treatment
 i) Limited dose capacity—The amount of pesticide that can be applied is limited by how much will actually stick to the
 ii) Limited duration of protection—The duration is often short due to the relatively small amount of biological agent (e.g. chemical) applied to the seed, dilution of the biological agent as the plant grows, and breakdown of the biological agent.
 iii) Limited shelf life of treated seed—Producing excess treated seed is undesirable because the shelf life of treated seed may be limited.

All three of these limitations may be overcome or significantly reduced through the inclusion of carnauba wax particles as a carrier for a biological agent, in this case dormant microorganisms that are applied to seeds. Under favourable conditions, the microorganisms grow and colonize the exterior of the developing seed or seedling. Biological agents may help in reducing seed decay, seedling diseases, or root rot.

The following tests are performed to examine the potential effect of the inclusion of carnauba wax particles.
Phase One—Isolate Cultures
1. Culture Maintenance Records are kept with each isolate sub-culture being assigned an accession number. All plates and slides relating to that sub-culture are labelled with an accession number.

In addition, permanent lactophenol (LP) mount slide are made from each of the original cultures and file for reference purposes No more than three generations of sub-culture occur before passaging through a living host and re-isolating in order to maintain the fitness of the organism.

Sub-cultures are stored for future use on Potato Dextrose Agar (PDA) at 4° c.

Each isolate is assigned an accession number and sub-cultures are labelled with that number.

DNA is extracted for identity verifications and stored at −20° C. A reference sample of the pure culture is stored on glycerol at −20° C. Upon completion of the experiment DNA identification of the culture is repeated to confirm that the organism has not mutated during the course of the work.
2. Culturing of the Causal Agent Isolation of a pathogenic fungus from diseased tissue into pure culture is one of the standard techniques in identifying and describing a disease. It is an essential step in proving the pathogenicity of previously un-encountered organisms.

Techniques commonly involve:
a. Surface-sterilisation treatment
b. Plating (possibly on selective medium) of samples of diseased tissue, with appropriate precautions.
c. Sub-culturing to get pure cultures.
3. Purification of Cultures Small disinfected root pieces of an artificially inoculated plant are cultured on water agar. The fungal colonies that appear most frequently are likely the target pathogen. Several saprophytes may also be present in infected plant tissues and they may grow into the medium with the principal pathogen. Routine surface-sterilisation consists of wiping the tissue with (or immersing in) 0.1% solution of sodium hypochlorite (NaOCl—sometimes referred to as "NaClO") followed by rinsing with sterile distilled water. To obtain a pure culture of the pathogen, a small sample is taken from the growing edge of a colony with a flamed loop or scalpel and streaked over the surface of a pre-poured plate of PDA. The inclusion of chloramphenicol (a bacteriostatic antimicrobial) at 30 mg/l reduces the risk of bacterial contamination. As the streak progresses over the agar, fungal spores are separated until single spores are obtained from which separate colonies will grow.

Repeat this procedure until pure cultures are obtained.

4. Single Spore Isolation

Single spore isolations are important to investigate pathogenic variability. An inoculum of spores is placed in a tube containing 10 ml of sterile water. This spore suspension is streaked along a marked line on the surface of a thin tap water agar medium, and incubated at 22° C. After 24 hr incubation, select germinated spores using a stereoscopic microscope and transferred one spore at a time to another agar plate.

5. Slide Preparation for Microscopic Examination and Reference

Identification of the pathogen, rather than the disease, will require microscopic examination of infected tissue. The tissue may be sectioned or surface scraped and then mounted in water/lactophenol. Fungal structures seen macroscopically may be separated from the host tissue to be examined and identified. Identification depends on spore formation and therefore infected material is incubated in a moist environment overnight prior to examination in order to encourage sporulation. Cotton blue stain is added to the lactophenol in order to highlight fungal structure. The specimen is placed in a drop of satin on a glass slide and gently warmed by passing through a low flame for a few seconds before mounting in lactophenol.

Whole mount sections can be cleared and stained for ease of identification using the following method:

Leaf disks are rendered clear by heating in tubes in lactophenol until clear (up to 20 minutes), without boiling. Stain by heating in 0.5% cotton blue in lactophenol on a slide for 5-10 minutes. Rinse thoroughly in lactophenol and mount in the same.

6. Growth and Media

Sub-cultures are assessed for growth and germination at a range of temperatures, 15° c., 22° c. and 29° c. A range of media is examined for suitability. Whilst PDA is generally suitable for most fungal species it has been found that use of a low nutrient agar, such as tap-water agar, reduce prolific growth and can encourage sporulation. Therefore PDA, tap-water agar, and a selective media from literature, Czapek's Dox agar (Dawson (1962) Saboutaudia 1. 214-219), are included within the assessment trials.

A 5 mm diameter disk is cut from the margin of an actively growing culture using a flamed cork borer. This is placed upside down in the centre of the pre-poured media plates. Five replicates are made for each media type and temperature (45 plates in total). Complete randomisation is applied to plates in each incubator. Plates are observed until one culture succeeds in completely covering the plate in any one media. At this point the following measurements are taken: fungus colony diameter, colour and margin. In addition, the level of sporulation is recorded.

Five 5 mm disks are cut from each plate using a flamed cork borer and suspended in 20 ml of distilled water (+0.05% Tween 20®). The sample is then sonicated for 2 minutes to release the spores and then vortexed to aid the formation of a uniform spore suspension. Samples are assessed for spore concentration using an Improved Neubauer haemocytometer using standard counting methodology.

The mean for each media type is calculated and ANOVA is applied to examine the results for significant differences.

Phase Two—In Vitro Studies:

1. Screen Microorganisms and Carnauba Wax to Determine Interactions

In order to explain effects observed the microorganisms, pathogens and antagonists, will be screened against carnauba wax to identify any carrier only effect. This will enable the determination of treatment effect as well as any synergy occurring as a result of the use of using an antagonist with carnauba wax particles.

a. Plates of appropriate media are used based on the findings of the experiment above. Air-milled carnauba wax is sterilised using the autoclave and then ground using a twin blade mill, producing particles with an approximate VMD of 130 µm. The sterilised media is then cooled to 50° C. (molten stage). The carnauba wax is then incorporated into the media. Two concentrations of carnauba wax are tested; 1 g/l and 10 g/l. A 5 mm diameter disk is cut from the margin of an actively growing culture using a flamed cork borer. This is placed upside down in the centre of the pre-poured media/carnauba wax plates. Five replicates are made for each concentration and incubated at the optimum temperature for growth/sporulation (as determined in previous experiment). Growth rates and characteristics are compared to the controls using data from the Growth and Media experiment above.

Differences are analysed using ANOVA.

b. Disks of the pathogen and antagonists are dusted with different carnauba wax treatments and put on appropriate media. The carnauba wax particles need to be free of microorganisms to be able to carry out this experiment. Growth of treated and untreated organisms is compared.

2. Investigate Antagonist Action Against Pathogens i. Effect of Antagonists on Viability of *R. solani* Mycelium (In Vitro Assay I)

All antagonistic isolates are tested in a dual culture assay against pathogenic fungi on PDA or alternative pre-defined media. Agar plugs of *R. solani* and the antagonist isolate to be tested are arranged 7 cm apart on 9 cm agar plates. Inhibition zones and zones of overlapping are assessed after 7 days incubation at 19° C., 25° C. and 31° C. Where an antagonist overgrows the mycelium of *R. solani*, the zone of hyphal interaction between both is investigated microscopically (100×). Fungal strains without a microscopically visible effect on mycelium of *R. solani* are excluded from further experiments. Furthermore, the viability of *R. solani* in the region of interaction is tested by transfer of mycelial discs onto water agar plates 5 days after first contact. The *R. solani* mycelium is assessed as viable when the growth of typical hyphae is observed microscopically (100×). Each experiment is repeated three times with three samples per replicate.

ii. Effect of Antagonists on Germination of *R. Solani* Sclerotia Produced In Vitro (In Vitro Assay II)

Sclerotia of *R. solani* of uniform size are placed on a 6 day old culture (PDA, 20° C.) of the fungal antagonist. After incubation for 14, 28 and 35 days at 20° C., eight sclerotia per replicate (three replicates per antagonist) are transferred from the agar plate onto water agar. Mycelial growth from these sclerotia is assessed under a light microscope (100×).

3. Confirmation of Pathogenicity

Steps to perform Koch's postulates (Koch 1890, criteria designed to establish a causal relationship between a causative microbe and a disease)

a) Describe the symptoms expressed by the diseased crop plants.
b) Isolate the suspected pathogen—the same cultures should be isolated from plants with similar symptoms
c) Obtain a pure culture and use it to inoculate healthy plant material.
d) Observe the symptoms expressed by the inoculated plants—symptoms should be the same as those observed originally in the crop plants.
e) Re-isolate the pathogen from the newly diseased material. The culture should be the same as the original purified culture.

i. Indirect Application—Plant

Using healthy plants—soil can be inoculated directly using a spore suspension made from a pure agar culture or from a culture grown in flasks. A fungal spore or bacterial suspension can be added post-emergence so that the root system is drenched by the suspension. Plants are then observed over 7 days and symptoms recorded. Koch's Postulates are applied in order to confirm that the symptoms relate to the inoculated pathogen.

ii. Direct Application—Seed

Inoculum for preparing spore suspensions is grown on water agar containing sterile seeds. Fungal spores and hyphae or bacterial spore and vegetative growth are scraped from the colony and transfer to sterile water. This spore suspension will then be applied to seeds and mixed to ensure a uniform distribution. Seeds are then:

Placed on moist filter paper and incubated at optimum growth temperature for 5 days.

sown in heat sterilised potting compost and incubated in a propagator at optimum growth temperature for 7 days Symptom expression and germination is recorded for both sets of experiments and Koch's postulates applied 4. Carnauba Wax/Antagonist Co-Location Analysis A dry powder formulation of spores is produced using a spore separator. Moisture content of the formulation is reduced to below 5% using a dehumidifier and silica beads. Spore concentration is determined using a Neubauer haemocytometer and standardised counting methodology.

Steps in Air Milling in Boyes Micronisation Process (for carnauba wax particles with a VMD of approx. 15 µm and 75 µm, respectively)

1. 2 kg carnauba wax blocks are first kibbled into approximately 4 to 6 mm pieces in a KT Handling Ltd Model 04 kibbler (serial no. 729/C) following the manufacturer's instructions.
2. The kibbled pieces are then passed through an Apex Construction Ltd Model 314.2 Comminuting Mill (serial no. A21306) and reduced further in size to a range of 250 to 300 um.
3. The comminuted particles are then passed through a Hosokawa Micron Ltd Alpine 100AFG jet mill (serial no. 168092) following the manufacturer's instructions, setting the mill at a suitable speed (a speed of 8000 rpm for particles having a VMD of 15 µm or at a speed of 2500 rpm for particles having a VMD of 75 µm), with a positive system pressure of 0.03 bar.
4. The grinding air is to be kept to 6 bar, the system rinsing air flow and Classifying Wheel gap rinsing air are both to be set at a minimum of 0.5 bar and no more than 0.75 bar, the cleaning air filter is to register a delta of no more than 5 bar to achieve a final particle size with a VMD of 15 um or 75 µm as required.

Entostat was combined with soya bean seed at three loadings (see below).

Two sizes of carnauba wax particle having VMDs of 15 µm and 75 µm, respectively, are examined in combination with the spore formulation at two different ratios (1:3, 2:2).

Samples of the carnauba wax/spore mixture are analysed using electron photomicroscopy to determine the co-location effect. Any variation observed is recorded.

In addition, both sizes of carnauba wax referred to, are mixed with a homogenised sample of mycelium and examined as described above.

5. Carnauba Wax Particle Loading

Carnauba wax particle adhesion to seeds is approximated through the use of photomicroscopy (qualitative) and fluorometric analysis (quantitative). Two sizes of carnauba wax particles (with 1% glo-brite) are used having a VMD of 15 µm and 75 µm, respectively. Four combinations: Two ratios of carnauba wax/spore formulation, together with one mycelial and a vehicle control (carnauba wax only), makes a total of eight treatments. Treatments are applied to 10 g of seed and replicated three times. Three subsamples are taken from each replicate and the mean used in analysis.

For fluorometric analysis three 1 g samples are each added to 5 ml of ethanol and sonicated to aid the release of the carnauba wax particles from the seeds. Samples are analysed using a Perkin Elmer L55 Fluorometer (Perkin Elmer, Ma, USA). Statistical analysis of variation between treatments is performed using ANOVA.

Seed size and architecture varies greatly between crop species and this influences application rates and method. A homogeneous mix is attained through tumbling seed and carnauba wax formulation in a cylinder, adapted to produce lateral mixing/tumbling through the inclusion of angled interior vanes, placed on a Wheaton roller for 5 minutes.

Phase Three—In Vivo:

*R. solani*, together with the most successful antagonist model is used in a series of in vivo experiments. The basic design is a split-plot experiment with temperature being the main plot factor (19° C., 25° C. and 31° C.) and carnauba wax/antagonist ratio (3 treatments:2× spore, 1× mycelial) being the sub-plot. Four homogeneous mixes of each treatment are prepared using the method described above and these represent the replicates.

Treatments:
1) Application rate 1—$7.5 \times 10^6$ conidia $kg^{-1}$
2) Application rate 2—$7.5 \times 10^8$ conidia $kg^{-1}$
3) Application 3—Mycelia
4) Control 1—Vehicle control (Carnauba wax only)
5) Control 2—no treatment Mixes (true replicates): A, B, C, D Subsamples of each mix: α, β, γ

Mixes and treatments are arranged according to a Randomised Complete Block design Pot Studies Each temperature (growth chamber) contains 60 plant pots.

Treated seed is sown in accordance with supplier's recommendation. Soil/compost (1:1 John Innes No. 2 and Potting compost) is heat sterilised prior to inoculation with 10 ml of *R. solani* spore suspension and thoroughly mixed before sowing.

Plants are placed in the growth chambers for a period of 21 days with observations of symptom expression made every 48 hours post emergence. Water is applied through capillary matting twice daily.

After 21 days plants are removed from their pots and the following assessment measurements taken:
% germination
% pre-emergence damping off
% post-emergence damping off
Root weight
Shoot weight In addition, symptom expression is assessed based on a damage scale.

Means of the measurements taken from the subsamples α, β, γ are compared for each treatment using ANOVA.

Samples are taken from 5 plants exhibiting symptoms and Koch's Postulates applied to confirm the causal organism (by comparison to the reference slide of the master culture). The experiment is repeated.

Second Example

Control of *Phytophthora* sp. [United Kingdom National Culture Collection (UKNCC)] on soya bean (*Glycine max*) by means of seed treatments using metalaxyl.
Experimental Design—as Pot Study Above Carnauba wax is melted using copper pans. During cooling metalaxyl is added at 1% of the mass of the carnauba. This mixture is allowed to solidify before chipping and processing through a mill as described above to produce particles with a VMD of 25 microns.
Treatments for the Pot Study—
Control 1—Vehicle control (Carnauba wax only)
Control 2—no treatment
Treatment 1—1% metalaxyl carnauba wax at 17 g per kg of seed
Treatment 2—1% metalaxyl carnauba wax at 5 g per kg of seed
Assessment and analysis as with previous Pot Study Third Example Control of Seed Corn Maggot (*Delia platura*), of Soya Bean (*Glycine max*) Using Seed Treated with Thiamethoxam Experimental Design—as Per the Pot Study of Example 1, Above Carnauba wax is melted using copper pans. During cooling thiamethoxam is added at 1% of the mass of the carnauba. This mixture is allowed to solidify before chipping and processing through a mill as descibed above to produce particles with a VMD of 25 μm.
Treatments for the Pot Study
Control 1—Vehicle control (Carnauba wax only)
Control 2—no treatment
Treatment 1—1% thiamethoxam carnauba wax at 4.2 g per kg of seed
Treatment 2—1% thiamethoxam carnauba wax at 1.3 g per kg of seed Empty pots are lined with a nylon mesh screening material before filling with potting soil. A wire frame is constructed and the nylon meshed tied off over the frame to provide a caged experimental arena designed so that the insect cannot escape the treated area.

Seeds are allowed to germinate for three days before adding five $3^{rd}$ instar larvae to the soil surface of each pot before resealing the mesh cage.

Observations are made over 21 days.
Plants are assessed for:
% germination
Damage
Root weight
Shoot weight Suppression of Causal Agents of Fungal Disease in Soya Bean (*Glycine max*) Using a Seed Coating Comprised of *Trichoderma* sp. And Carnauba Wax Particles The potential for *Trichoderma* sp. (Ascomycota) as a biocontrol agent in the defence against plant pathogens is known.

*Trichoderma* hyphae are capable of penetrating the hyphae of other fungi and extracting nutrients from within, resulting in the suppression and eventual death of the host. *Trichoderma* exhibits rapid mycelial growth and is capable of out-competing other fungi for nutrients.

There are several commercially available formulations of *Trichoderma* marketed as crop protection products. These are commonly supplied as a wettable powder formulation and applied to the area of cultivation as a drench. The disadvantage of this form of application is that it is necessary to treat the entire cultivation area, whereas it is the region immediately surrounding the seed or plant that requires the treatment. The larger the number of conidia delivered to this area the greater the level of control they are able to impart. Therefore a targeted application system able to deliver sufficient conidia to the required area offers a distinct advantage in the use of *Trichoderma* over conventional applications.

Experimental Aim: To Assess the Potential Use of Entostat as a Seed-Coating Technology for the Delivery of Beneficial Microbes
Methods
Steps in Air Milling in Boyes Micronisation Process (for carnauba wax particles with a VMD of approx. 10 μm)
1. 2 kg carnauba wax blocks are first kibbled into approximately 4 to 6 mm pieces in a KT Handling Ltd Model 04 kibbler (serial no. 729/C) following the manufacturer's instructions.
2. The kibbled pieces are then passed through an Apex Construction Ltd Model 314.2 Comminuting Mill (serial no. A21306) and reduced further in size to a range of 250 to 300 um.
3. The comminuted particles are then passed through a Hosokawa Micron Ltd Alpine 100AFG jet mill (serial no. 168092) following the manufacturer's instructions, setting the mill at a speed of 12,500 rpm, with a positive system pressure of 0.03 bar.
4. The grinding air is to be kept to 6 bar, the system rinsing air flow and Classifying Wheel gap rinsing air are both to be set at a minimum of 0.5 bar and no more than 0.75 bar, the cleaning air filter is to register a delta of no more than 5 bar to achieve a final particle size with a VMD of 9.7 μm.

Entostat was combined with oilseed at three loadings (see below).
1. Baseline data: seed coating techniques
  1.1. Seed Coating. *Trichoderma harzianum* (containing $7.75 \times 10^9$ colony forming units $g^{-1}$ Sylvan Bio, Loches, France) with a germination percentage of 95% was applied to soya bean (var. *Pripyat*) supplied by Soya UK, (West End, Hampshire) using carnauba wax particles with a VMD of 9.7 μm. A target loading was set at $10^5$ conidia per seed based on information obtained from literature.

Carnauba particles were mixed with the dry conidia powder at different ratios and applied 0.01 g (0.2% by mass) directly to dry seed, 5 g of seeds per concentration. For each concentration, four batches of 10 seeds were used for evaluation of conidia loading.

Conidia to carnauba ratios used were:

100% Conidia, 50% Conidia, 25% Conidia and 9% Conidia with the remainder in each case being made up of carnauba wax particles.

1.2. Enumeration. Direct enumeration to determine conidia loading of seeds was done through the use of a haemocytometer (Improved Neubauer, Hawksley, Lancing, UK).

Inoculum: Preparation of suspension.

Propagules are usually formulated in a water carrier, although those with hydrophobic cell walls (such as *Trichoderma*) are not readily suspended in water. To uniformly suspend hydrophobic propagules in water it is necessary to sonicate and/or use mechanical suspension methods. Mechanical suspension of propagules using micropestles provides good suspension of conidia in water without causing damage to cells. A surfactant may also facilitate suspension of propagules (Tween20 at 0.05%). To suspend hydrophobic conidia, harvested conidia are placed in a 1.5 ml microcentrifuge tube, ≈0.5 ml of sterile water is added to the tube, the micropestle is inserted into the tube, and the conidial mass is gently agitated with the micropestle by hand. The micropestle is the attached to the motor (e.g. Kontes, Argos pellet pestle motor) and the suspension is vigorously agitated while moving the pestle in and up and down, and side to side motion, circa. 30 seconds. Since the haemocytometer method does not distinguish between viable and non-viable propagules, it is necessary to determine spore viability so that doses can be prepared on the basis of viable propagules.

Seed washes and enumeration of *Trichoderma* loadings were done on 4 batches of seeds per treatment. Inoculum was washed from seeds by placing into 1 ml sterile 0.05% $Tween^{20}$ (or substitute—similar non-ionic surfactant/dispersal agent) in a Eppendorf tube and vortexing for 30 seconds to remove conidia from the seed surface. Samples were then sonicated for two minutes to break up any conidial clumping. Counts obtained were used to calculate the mean conidia loading of seed coated with the various treatments. Results obtained using 100% conidia powder were used as a benchmark and the conidia/carnauba combination powders compared against it as a determination of efficiency of loading.

Confirmation of conidial viability was achieved by dilution plating on *Trichoderma* Specific Media (TSM) (see below). A dilution series was set up and duplicate plates inoculated from the series. Colony Forming Units (CFU) counts were made after 7 days, allowing inoculum levels on seeds to be quantified. In addition, fresh, unused conidia were plated to provide a comparison of before and after seed application.

Germination percentage was also measured. A satisfactory density of conidia was obtained by spreading approximately $10^6$ conidia in 100 μl on the media in a 9 cm petri dish. Conidia were incubated in the dark at 25° C. for five days, and the area to be observed was then fixed using lactophenol. Phase contrast microscopy using an inverted compound microscope enabled sufficient examination of the conidia.

Conidia were considered viable if germtube lengths were two times the diameter of the propagule in question. Numbers of germinated and non-germinated conidia in arbitrarily-selected fields of view or in parallel transects, defined with an ocular micrometer, were counted. A minimum of 300 conidia were counted to provide an accurate estimate. It is desirable to determine the viability of propagules on replicate cultures and at various positions on the same plate.

This allowed calibration of the seed-coating techniques to obtain similar levels of *Trichoderma* loadings on the seeds for each coating method.

1.3. Seed Germination. One batch (5 seeds) of seeds from each treatment was placed on seed test paper (Whatman 181) in a 9 cm Petri dish. Dishes were sealed with Parafilm and held at 20° C. for 7-10 days and germination rate determined. This was repeated with untreated seed.

*Trichoderma* Selective Media (adapted from Williams, Clarkson et al 2003) was prepared as follows:

For 1000 m1

Basal Medium Ingredients:

| | |
|---|---|
| 0.2 g $MgSO_4$ | 3.0 g glucose |
| 0.9 g $K_2HPO_4$ | 0.15 g rose bengal |
| 0.15 g KCl | 20 g agar |
| 1.0 g $NH_4NO_3$ | 950 ml distilled water |

Basal Medium Process

Mix liquid ingredients with all solid ingredients, except the agar in a 1 L Erlenmeyer flask. Add the 20 g agar and stir or shake. Plug with cotton wool and cover with foil. Autoclave.

Biocidal Medium (Per Liter)

0.25 g crystallized chloramphenicol 0.2 g quintozene 0.2 g captan 1.2 ml propamocarb (Previcur)

50 ml sterile distilled water

Seed Weight

Used as a measure of the homogeneity of the seed batch. Eight replicates of 25 seeds are weighed and the coefficient of variation (Cv) recorded. This coefficient should not exceed a value of 5. If it does then the procedure is repeated and the mean of all 16 samples used to calculate the number of seeds per gram.

| Crop | Mean Weight (g) | SD | Cv | TGW (g) |
|---|---|---|---|---|
| Soybean | 3.011 | 0.145 | 4.809 | 12.455 |

Results

Direct Enumeration Counts Using Haemocytometer

Initial Spore Density of *Trichoderma harzianum* dry spore preparation (at 5% moisture content), determined using haemocytometer, was $7.75\times10^9$ spores $g^{-1}$ (n=4, ±$2.6\times10^7$ 95% CL).

Spore Counting of Seed Wash

| Variable | Spore % | N | Mean | SE Mean |
|---|---|---|---|---|
| SporeCount | 9 | 4 | 1037500 | 37942 |
|  | 25 | 4 | 3912500 | 336882 |
|  | 50 | 4 | 5562500 | 281643 |
|  | 100 | 4 | 2355000 | 160857 |

See FIG. 1.

There was a clear and statistically significant difference between the mean spore counts per seed achieved by the different treatments as determined by one-way ANOVA ($F(3,12)=69.53$, $p=<0.001$). All treatments exceeded the target of $10^5$ spores seed$^{-1}$.

| % Spores | Mean Spore Count Seed$^{-1}$ | *Expected Spore Count | As a % of 100% Treatment | **As a % of Expected | t value | p value |
|---|---|---|---|---|---|---|
| 100% | 2355000 | n/a | n/a | n/a | n/a | n/a |
| 50% | 5562500 | 1177500 | 236% | 472% | 15.57 | 0.001 |
| 25%* | 3912500 | 588750 | 166% | 665% | 9.87 | 0.002 |
| 9% | 1037500 | 211950 | 44% | 490% | 21.76 | <0.001 |

*Expected Spore Count is calculated from the mean spore count achieved by the 100% Treatment, assuming a perfect distribution. Therefore the 50% Treatment would be expected to result in half the spores of the 100% Treatment, and so on.
**Essentially a measure of improvement in spore adhesion efficiency.

The addition of Entostat appears to improve the efficiency of spore adhesion to seed as the actual mean counts significantly exceed the expected results based on the 100% spore treatment (t-test).

Germination Determination

Mean Conidia Germination (from a Sample of 300)
Fresh conidia 276.75±5.97, n=4

Seed wash conidia 283.75±4.48, n=4

There was no statistically significant difference between the viability of fresh conidia and those washed from seeds as determined by one-way ANOVA (F(1,6)=1.69, p=0.241).

Enumeration Estimate from CFU Counts

Comparison of Haemocytometer and CFU (Corrected for Dilution) Counts

| Treatment | N | Mean | SE Mean | Grouping (using Tukey method) |
|---|---|---|---|---|
| 100CFU | 4 | 2291875 | 61300 | A |
| 100Haemo | 4 | 2355000 | 160857 | A |
| 50CFU | 4 | 5592500 | 279743 | B |
| 50Haemo | 4 | 5562500 | 281643 | B |
| 25CFU | 4 | 4160000 | 131735 | C |
| 25Haemo | 4 | 3912500 | 336882 | C |
| 9CFU | 4 | 1050000 | 53580 | D |
| 9Haemo | 4 | 1037500 | 37942 | D |

Means that do not share a letter are significantly different.

There was a statistically significant difference between groups as determined by one-way ANOVA (F(7,24)=83.51, p=<0.001). A Tukey post-hoc test revealed significance was as a result of differences in the spore % rather than the counting method applied.

Additional Work

*Trichoderma harzianum* was tested alongside Entostat on soya bean. The study was not replicated therefore statistical analysis has not been applied.

Haemocytometer counts, method as described above, were used to assess the spore quantity in the wash from treated seed using 0.05% Tween[20] solution.

Spore density of *Trichoderma* was $10^9$ spores per gram

Thousand seed weight of soybean used was 190.4 g

| Treatment | Spore Count per seed |
|---|---|
| *Trichoderma*: 0.016 g | $3 \times 10^5$ |
| *Trichoderma*: 0.016 g + Entostat: 0.034 g | $3.3 \times 10^5$ |
| **Trichoderma*: 0.034 g + Entostat: 0.066 g | $4.2 \times 10^5$ |
| *Trichoderma*: 0.034 g + Entostat: 0.034 g | $7.5 \times 10^5$ |
| ***Trichoderma*: 0.034 g + Entostat: 0.066 g | $5.4 \times 10^5$ |
| *Trichoderma*: 0.034 g + Entostat: 0.066 g | $8.4 \times 10^5$ |
| *Trichoderma*: 0.034 g | $4.2 \times 10^5$ |

**Trichoderma* was added first
***Trichoderma* was mixed with Entostat before adding to the seed Adding spores to Entostat before mixing into the seed appears to improve the adhesion of spores to the seed.

The use of Entostat at 0.066 g with *Trichoderma* at 0.034 g increased the number of spores counted per seed two-fold when compared to *Trichoderma* alone.

Summary

Soybean seed can be coated with *Trichoderma* spores in excess the target $10^5$ spores $seed^{-1}$ for all treatments.

Use of Entostat increases the efficiency of spore delivery as a result of a reduction in wasted or lost spores.

The germination viability of the spores was unaffected by their use as a seed coating.

Enumeration through direct counting of spores using a haemocytometer or through the use of CFU counting gives statistically similar results and therefore either method may be used once germination viability has been proved unaffected by the treatment.

The above-described method for soya bean as provided above is used to assess the delivery efficiency of spores by Entostat to seeds of peas, bean, lentils, and lupin. Similar results are obtained.

Effects of Seed Coating on Disease Suppression

Seeds are coated with *Trichoderma* using water or Entostat to achieve loadings of ca. $10^5$ and $10^6$ CFUs $seed^{-1}$. Water treatments are suspensions of spores in sterile water in which the seed samples are soaked for one hour. Seeds are then dried back, a likely commercial scenario, or sown wet coated. Entostat is applied at ratios of 3:1, and 9:1, Entostat to spores respectively. Seed treatment methods are then compared for their ability to protect germinating soya bean seedlings from *Rhizoctonia solani*, the causal agent of root rot disease in soya bean.

Inoculation of seeds with *Trichoderma*. Soya bean cv. *Pripyat* is inoculated as follows (target concentration per seed):

1) *Trichoderma* at $10^5$/seed using a water suspension (wet coating)
2) *Trichoderma* at $10^6$/seed using a water suspension (wet coating)
3) *Trichoderma* at $10^5$/seed using a water suspension (dry coating)
4) *Trichoderma* at $10^6$/seed using a water suspension (dry coating)
5) *Trichoderma* at $10^5$/seed using Entostat at 3:1
6) *Trichoderma* at $10^6$/seed using Entostat at 3:1
7) *Trichoderma* at $10^5$/seed using Entostat at 9:1
8) *Trichoderma* at $10^6$/seed using Entostat at 9:1
9) No *Trichoderma*, water only
10) No *Trichoderma*, Entostat only
11) Seed only Enumeration.

*Trichoderma* is quantified using standard dilution plating methods on *Trichoderma* specific media. This confirms CFU loadings per seed for treatments 1-8. Dilution platings are carried out in duplicate.

Rhizoctonia Bioassay
Inoculum Preparation—

Rhizoctonia sp., known to be pathogenic on many members of the Leguminosea family, such as soybean, clover, peas, beans, lentils, and lupins, is grown on PDA plates from stock cultures, and incubated at 20° C. to produce actively growing colonies. Agar plugs are removed from the plates and used to inoculate sterilised (autoclaved at 121° C. for 20 mins) John Innes No. 2 potting mix (80% moisture content; 60 g) mixed with potato cubes (2 mm$^2$, 25 g) in 500 ml Erlenmeyer flasks. Flasks are incubated at 20° C. for 14 days. Inoculum levels in the medium are quantified using a dilution plating method.

Effectiveness of seed treatment on *Rhizoctonia*. Seeds are sown into individual cells of seed trays containing *Rhizoctonia*-inoculated medium (approx. 15 ml/cell). Four replicate batches of ten seeds per treatment are planted into the cells. Once sown, the trays are placed in a plant growth chamber (Weiss Gallenkamp Fitotron SG120) at 20° C. with ca. 16 h lighting. Cells are bottom watered. The number of seedlings surviving is recorded every 3 days for 21 days.

Time to emergence, percentage successful emergence and percentage plants expressing symptoms (including lesions and cankers) are recorded and the results analysed.

The described method for soya bean as provided above is used to assess time to emergence, percentage successful emergence and percentage plants expressing symptoms are recorded for seeds of lupin, clover, peas, lentils, and beans. Similar results as obtained for Entostat treated and untreated soya bean seed are obtained. Differences in Entostat treated seed and untreated seed are observed.

The invention claimed is:

1. A soybean seed product form comprising:
   i) a coating composition in powder form, the coating composition is consisting of:
   (1) solid particles made throughout of at least one organic carrier material and having a volume mean diameter of ≥5 μm, wherein the carrier material is selected from waxes having a melting point of ≥50° Centigrade, and
   (2) one or more biological agents that possess an activity against at least one pathogen of a soybean plant; and
   ii) a soybean seed,
   wherein the soybean seed is coated with the composition of i).

2. The soybean seed product form according to claim 1, wherein the particles have a volume mean diameter in the range of 8 to 200 μm.

3. The soybean seed product form according to claim 1, wherein the biological agent is selected from a chemical agent and a live biological agent or is a mixture thereof.

4. The soybean seed product form according to claim 1, wherein the biological agent is selected from chemical fungicides, arthropodicides and bactericides or is a mixture of two or more thereof.

5. The soybean seed product form according to claim 1, wherein the biological agent is selected from fungicides, insecticides and acaricides.

6. The soybean seed product form according to claim 5, wherein the fungicides are selected from acyl amino acid fungicides, pyrrole fungicides and strobilurin fungicides or are mixtures of two or more thereof.

7. The soybean seed product form according to claim 4, wherein the arthropodicides are insecticides selected from nicotinoid insecticides or are mixtures of two or more thereof.

8. The soybean seed product form according claim 1, wherein the organic carrier material is selected from carnauba wax, beeswax, montan wax, Chinese wax, shellac wax, spermaceti wax, candelilla wax, castor wax, ouricury wax and rice bran wax or is a mixture of two or more thereof.

9. The soybean seed product form according to claim 8, wherein the particles are carnauba wax particles.

10. The soybean seed product form according to claim 1, wherein the biological agent is at least one biological antagonist present in the form of bacterial spores and/or fungal spores located on the surface of the said particles.

11. A method of coating soybean seed with a coating composition that consists of an organic carrier material in the form of particles of wax having a volume mean diameter of ≥5 μm, wherein the wax is selected from waxes having a melting point of ≥50° Centigrade, and a biological agent that has an activity against a soya bean plant pathogen selected from a fungal pathogen, a bacterial pathogen and an arthropod pathogen, the method comprising adding the biological agent to the organic carrier material, wherein the organic carrier material is in a dry particulate form, mixing the two together and applying the resulting composition to soybean seeds.

12. The method according to claim 11, wherein the coating composition is applied in dry particulate form to soya bean seeds.

13. The method according to claim 11, wherein the wax is selected from carnauba wax, beeswax, montan wax, Chinese wax, shellac wax, spermaceti wax, myricyl palmitate, cetyl palmitate, candelilla wax, castor wax, ouricury wax, wool wax, sugar cane wax, retamo wax and rice bran wax or is a mixture of two or more thereof.

14. The method according to claim 11, wherein the organic carrier material is carnauba wax.

15. The method according to claim 11, wherein the biological agent is selected from insecticides, acaricides, fungicides, bactericides and live biological agents.

16. The method according to claim 11, wherein the biological agent is selected from fungicides and insecticides.

17. The method according to claim 16, wherein the fungicide is selected from acyl amino acid fungicides, pyrrole fungicides, and strobilurin fungicides or is a mixtures of two or more thereof.

18. The method according to claim 16, wherein the biological agent is selected from nicotinoid insecticides or is a mixture of two or more thereof.

19. The soybean seed product form according to claim 2, wherein the biological agent is selected from a chemical agent and a live biological agent or is a mixture thereof.

20. The soybean seed product form according to claim 1, wherein the particles are applied directly to the seed.

21. A soybean seed product form comprising:
   i) a coating composition in powder form, the coating composition is consisting essentially of:
   (1) particles consisting of at least one organic carrier material and having a volume mean diameter of ≥5 μm, wherein the carrier material is selected from waxes having a melting point of ≥50° Centigrade, and
   (2) one or more biological agents that possess an activity against at least one pathogen of a soybean plant; and
   ii) a soybean seed,
   wherein the soybean seed is coated with the composition of i).

* * * * *